(12) United States Patent
Kim et al.

(10) Patent No.: US 10,473,648 B2
(45) Date of Patent: Nov. 12, 2019

(54) BIOSENSOR

(71) Applicant: ELECTRONICS AND TELECOMMUNICATIONS RESEARCH INSTITUTE, Daejeon (KR)

(72) Inventors: Young Jun Kim, Daejeon (KR); Wan Joong Kim, Daejeon (KR); Bong Kyu Kim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 110 days.

(21) Appl. No.: 15/630,835

(22) Filed: Jun. 22, 2017

(65) Prior Publication Data

US 2018/0188238 A1 Jul. 5, 2018

(30) Foreign Application Priority Data

Jan. 2, 2017 (KR) ................. 10-2017-0000434

(51) Int. Cl.
| | |
|---|---|
| G01N 3/52 | (2006.01) |
| G01N 33/52 | (2006.01) |
| A61B 5/145 | (2006.01) |
| A61B 5/16 | (2006.01) |
| G01N 7/02 | (2006.01) |
| C12Q 1/00 | (2006.01) |

(52) U.S. Cl.
CPC ......... *G01N 33/52* (2013.01); *A61B 5/14532* (2013.01); *A61B 5/165* (2013.01); *C12Q 1/006* (2013.01); *G01N 7/02* (2013.01)

(58) Field of Classification Search
CPC .......... G01N 33/52; G01N 7/02; A61B 5/165; A61B 5/14532; C12Q 1/006
See application file for complete search history.

(56) References Cited

U.S. PATENT DOCUMENTS

| | | | |
|---|---|---|---|
| 7,981,689 B2 * | 7/2011 | Matsumoto | B01L 3/502715 |
| | | | 422/401 |
| 8,169,006 B2 | 5/2012 | Kim et al. | |
| 9,028,661 B2 | 5/2015 | Bartling et al. | |
| 2003/0190608 A1 * | 10/2003 | Blackburn | B01J 19/0093 |
| | | | 435/6.11 |
| 2010/0144020 A1 | 6/2010 | Kim et al. | |

(Continued)

FOREIGN PATENT DOCUMENTS

| | | |
|---|---|---|
| JP | 2010-133921 A | 6/2010 |
| JP | 2012-88326 A | 5/2012 |

(Continued)

OTHER PUBLICATIONS

Ghazal et al "Recent advances in X-ray compatible microfluidics for applications in soft materials and life sciences" Lab Chip, 2016, 16, 4263 (Year: 2016).*

(Continued)

*Primary Examiner* — Dennis White (57) ABSTRACT

Provided is a biosensor including a capillary unit having a capillary channel therein and a reagent disposed in the capillary channel, the reagent being configured to develop colors in a sample, and a measuring unit configured to measure a degree of color development of the sample in the capillary channel.

10 Claims, 7 Drawing Sheets

(56) References Cited

U.S. PATENT DOCUMENTS

| | | | |
|---|---|---|---|
| 2013/0122485 A1 | 5/2013 | Hong | |
| 2015/0147769 A1 | 5/2015 | Kim et al. | |
| 2015/0168361 A1* | 6/2015 | Shimayama | C12Q 1/00 435/15 |
| 2016/0310948 A1* | 10/2016 | Nowakowski | C12Q 1/6816 |
| 2016/0341724 A1 | 11/2016 | Kim et al. | |

FOREIGN PATENT DOCUMENTS

| | | |
|---|---|---|
| KR | 10-2014-0040100 A | 4/2014 |
| KR | 1020150059413 A | 6/2015 |
| KR | 10-2016-0047391 A | 5/2016 |
| KR | 1020160136223 A | 11/2016 |

OTHER PUBLICATIONS

Masaki Yamaguchi et al., "Performance evaluation of salivary amylase activity monitor", Biosensors and Bioelectronics 20, 2004, pp. 491-497, Elsevier B.V.

\* cited by examiner

BIOSENSOR

CROSS-REFERENCE TO RELATED APPLICATIONS

This U.S. non-provisional patent application claims priority under 35 U.S.C. § 119 of Korean Patent Application No. 10-2017-0000434, filed on Jan. 2, 2017, the entire contents of which are hereby incorporated by reference.

BACKGROUND

The present disclosure herein relates to a biosensor and more particularly, to a biosensor for examining such as a blood sugar level or a stress level, etc. using a degree of color development of a sample developed by a reagent.

A biosensor is a device capable of sensing an optical or electrical signal changing according to a selective reaction and combination between a biological receptor having a recognition function for a specific biomaterial and an analyte desired to analyze. In other words, the biosensor may check existence of biomaterials or analyze the biomaterials qualitatively or quantitatively. Here, an enzyme, antibody, or DNA etc. capable of selectively reacting or combining with a specific material is used as the biological receptor (namely, a sensing material). In addition, as a signal sensing method, the biomaterial may be detected and analyzed using various physicochemical methods such as an electrical signal change according to presence or absence of the analyte, or an optical signal change by a chemical reaction between a receptor and an analyte, etc.

SUMMARY

The present disclosure provides a biosensor capable of swiftly measuring and analyzing a biomaterial included in a sample.

Issues to be addressed in the present disclosure are not limited to those described above and other issues unmentioned above will be clearly understood by those skilled in the art from the following description.

An embodiment of the inventive concept provides a biosensor including: a capillary unit having a capillary channel therein and a reagent disposed in the capillary channel, the reagent being configured to develop colors in a sample; and a measuring unit configured to measure a degree of color development of the sample in the capillary channel.

In an embodiment, the reagent may be freeze-dried.

In an embodiment, the reagent may include a color-developing material configured to develop the colors in the sample.

In an embodiment, the sample may include an α-amylase, and the color-developing material may be 2-Chloro-4-nitrophenyl-α-D-maltotrioside.

In an embodiment, the reagent may further include a catalyst material configured to expedite a reaction of the color-developing material and the sample.

In an embodiment, the measuring unit may include: a light emitting unit configured to emit a light toward the capillary channel; and a light receiving unit configured to receive a light having passed through the capillary channel.

In an embodiment, the capillary unit may include: a first pin hole which is connected to the capillary channel and through which the light emitted from the light emitting unit passes; and a second pin hole which is connected to the capillary channel and through which a light traveling toward the light receiving unit passes.

In an embodiment, the light emitting unit, the light receiving unit, and the first and second pin holes may be disposed on a virtual straight line.

In an embodiment, the biosensor may further include a temperature adjusting unit configured to adjust a temperature of the sample in the capillary channel, wherein the measuring unit further includes a temperature sensor configured to measure the temperature of the sample in the capillary channel.

In an embodiment, the temperature adjusting unit may include a Peltier device.

In an embodiment, the biosensor may further include a controller configured to calculate concentration information on a biomaterial included in the sample using the sample's color-development information measured by the measuring unit.

In an embodiment, the biosensor may further include a communication unit configured to transmit the calculated biomaterial concentration information to an external device.

In an embodiment, the communication unit may include at least any one of a Bluetooth communication module and a Wi-Fi communication module.

In an embodiment, one end of the capillary unit may have an inlet connected to the capillary channel.

Specific items of other embodiments are included in the detailed description and drawings of the present invention.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Advantages and features of the present invention, and methods for achieving the same will be cleared with reference to exemplary embodiments described later in detail together with the accompanying drawings. However, the present invention is not limited to the following exemplary embodiments, but realized in various forms. In other words, the present exemplary embodiments are provided just to complete disclosure the present invention and make a person having an ordinary skill in the art understand the scope of the invention. The present invention should be defined by only the scope of the accompanying claims. Throughout this specification, like numerals refer to like elements.

Example embodiments are described herein with reference to cross-sectional views and/or plan views that are schematic illustrations of example embodiments. In the drawings, the thicknesses of layers and regions are exaggerated for clarity. Thus, the regions illustrated in the figures are schematic in nature and their shapes may be not intended to illustrate the actual shape of a region of a device and are not intended to limit the scope of example embodiments. It will be understood that although the terms "first", "second", etc. may be used herein to describe various components, these components should not be limited by these terms. The terms are used only for distinguishing a constituent element from other constituent elements. Exemplary embodiments described and illustrated here include complementary exemplary embodiments thereof.

The terms and words used in the following description and claims are to describe embodiments but are not limited the inventive concept. As used herein, the singular forms "a," "an" and "the" are intended to include the plural forms as well, unless the context clearly indicates otherwise. It will be further understood that the terms "comprises" and/or "comprising" used herein specify the presence of stated components, operations and/or elements but do not preclude the presence or addition of one or more other components, operations and/or elements.

Unless otherwise defined, all terms (including technical and scientific terms) used herein have the same meaning as commonly understood by one of ordinary skill in the art to which the invention belongs. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Hereinafter, embodiments of the inventive concept will be described in detail with reference to the accompanying drawings.

Figure 1:
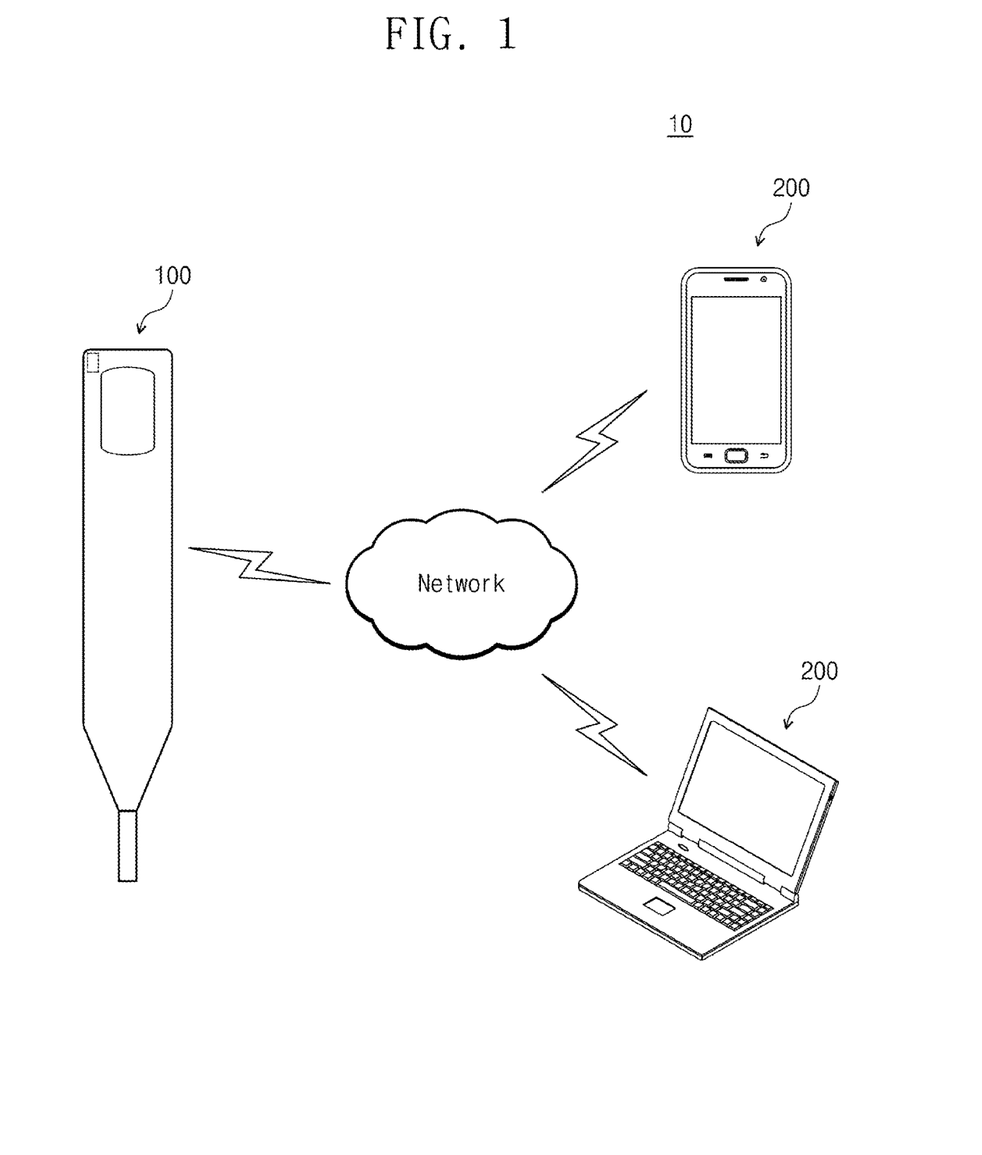
FIG. 1 is a schematic diagram for explaining a biomaterial analyzing system using a biosensor according to embodiments of the inventive concept.

FIG. 1 is a schematic diagram for explaining a biomaterial analyzing system using a biosensor according to embodiments of the inventive concept.

Referring to FIG. 1, a biomaterial analyzing system 10 according to embodiments of the inventive concept may examine whether a user has a disease and a user's health state using a biosensor 100. The biomaterial analyzing system 10 may include the biosensor 100 and an external device 200. A detailed description about the biosensor 100 will be provided later.

The external device 300 may be a device capable of performing wired and/or wireless communication through a network. The external device 200 may include a communication module (not shown). The communication module of the external device 200 may perform wired and/or wireless communication. The external device 200 may include a display unit (not shown). The display unit of the external device 200 may output information received from the biosensor 100. For example, the external device 200 may be a notebook or a smartphone, etc., but is not limited thereto.

Figure 2:
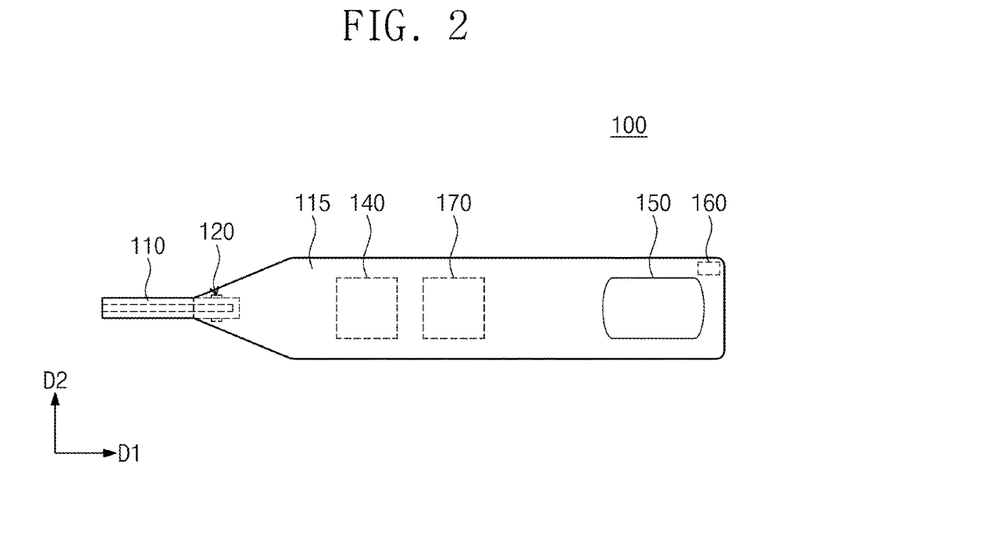
FIG. 2 is a plan view for explaining the biosensor of FIG. 1.
Figure 3:
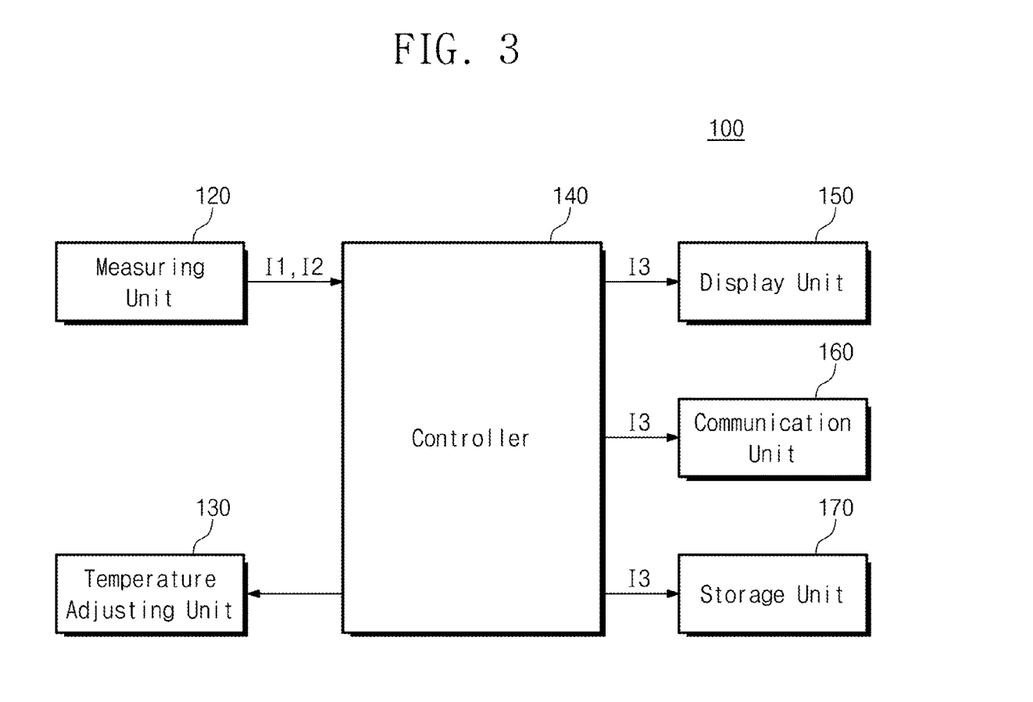
FIG. 3 is a block diagram for explaining the biosensor of FIG. 1.

FIG. 2 is a plan view for explaining the biosensor of FIG. 1. FIG. 3 is a block diagram for explaining the biosensor of FIG. 1.

Referring to FIGS. 2 and 3, the biosensor 100 according to embodiments of the inventive concept may collect a non-invasive sample (hereinafter sample) to acquire user's biomaterial concentration information. The sample may be urine, tear, snot, or saliva, etc., but is not limited thereto.

The biosensor 100 may include a capillary unit 110, a body unit 115, a measuring unit 120, a communication unit 160, and a controller 140. In addition, the biosensor 100 may further include a temperature adjusting unit 130, a display unit 150, and a storage unit 170.

The body unit 115 may provide an appearance of the biosensor 100. The body unit 115 may have a reception space therein. The body unit 115 may be connected to the capillary unit 110. For example, a part of the capillary unit 110 may be inserted into the body unit 115. The body unit 115 may be formed lengthily in a first direction D1, but is not limited thereto.

The capillary unit 100 may be disposed at one end of the body unit 115. According to an embodiment, the capillary unit 110 may be provided as a cylinder that is long in the first direction D1, but is not limited thereto. A detailed description about the capillary unit 110 will be provided in relation to FIG. 4.

The measuring unit 120 may measure a sample flowed in the capillary unit 110 to acquire various information on the sample. According to embodiments, the measuring unit 120 may acquire color development information I1 on the sample and/or temperature information I2 on the sample, etc., but is not limited thereto. The measuring unit 120 may transmit the color development information I1 on the sample and/or the temperature information on the sample to the controller 140. A detailed description about the measuring unit 120 will be provided in relation to FIG. 4.

The controller 140 may calculate a concentration of a biomaterial included in the sample (hereinafter, biomaterial concentration information) using the color development information I1. For example, the controller 140 may be a microprocessor, but is not limited thereto. In addition, the controller 140 may transmit the calculated biomaterial concentration information I3 to the communication unit 160, the storage unit 170 and/or the display unit 150. In addition, the controller 140 may control driving of the temperature adjusting unit 130. A detailed description about the controller 140 will be provided in relation to FIG. 4.

The communication unit 160 may transmit the biomaterial concentration information I3 received from the controller 140 to the external device 200. The communication unit 160 may include a communication module capable of performing wired and/or wireless communication. For example, the communication unit 160 may include at least any one of a Bluetooth communication module and a Wi-Fi communication module.

According to embodiments, the communication unit 160 may be connected to a network through the wireless communication. The communication unit 160 may transmit the biomaterial concentration information I3 to the external device 200 through the network. For example, the communication unit 160 may transmit the biomaterial concentration information I3 to the external device 200 through an Ethernet or the Internet, etc.

On the contrary, in another embodiment, the communication unit 160 may transmit the biomaterial concentration information I3 to the external device 200 without passing through the network. For example, the communication unit 160 may transmit the biomaterial concentration information I3 to the external device 200 through Bluetooth.

The storage unit 170 may store various pieces of data. For example, the storage unit 170 may store the biomaterial concentration information I3 and various pieces of information on the sample. According to embodiments, the storage unit 170 may be a memory.

The measuring unit 120, the communication unit 160, the storage unit 170, and the controller 140 may be disposed in the reception space of the body unit 115. Accordingly, the body unit 115 may protect the measuring unit 120, the communication unit 160, the storage unit 170, and the controller 140 from the external environment.

The temperature adjusting unit 130 may adjust a temperature of the sample flowed into the capillary unit 110. A detailed description about the temperature adjusting unit 130 will be provided in relation to FIG. 4.

The display unit 150 may output the biomaterial concentration information received from the controller 140. According to embodiments, the display unit 150 may be a touch screen, but is not limited thereto.

Figure 4:
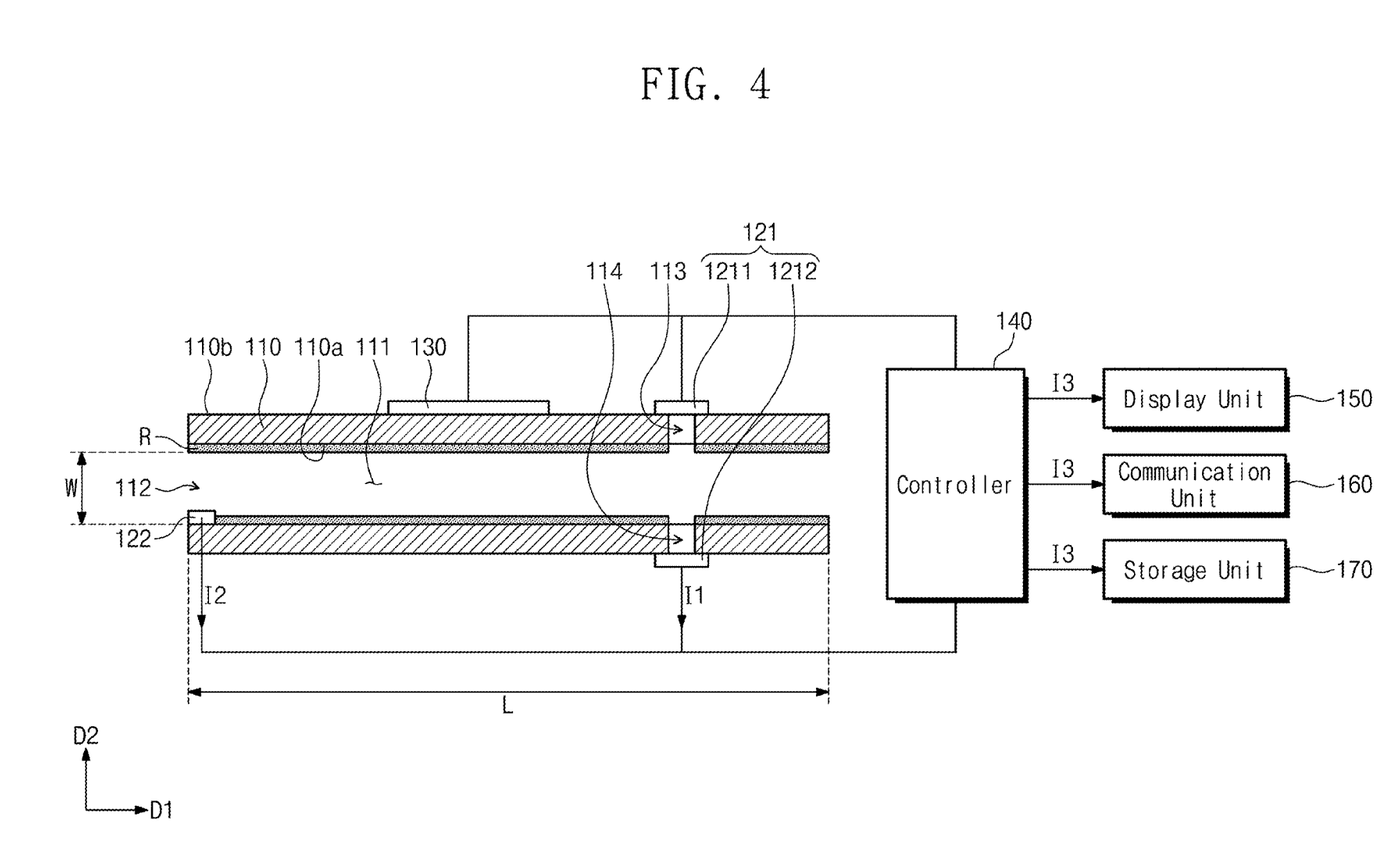
FIG. 4 is a schematic diagram for explaining the biosensor of FIG. 1.

FIG. 4 is a schematic diagram for explaining the biosensor of FIG. 1.

Referring to FIG. 4, the capillary unit 110 may have, at one end, an inlet 112 through which a sample is flowed in. In addition, the capillary unit 110 may have a capillary channel 111 therein. The capillary channel 111 may extend from the inlet 112 in the first direction D1. The capillary channel 111 may be connected to the inlet 112. According to an embodiment, the other end of the capillary unit 110 may be open, but is limited thereto. Alternatively, the other end of the capillary unit 1110 may not be open.

The length L of the capillary channel 111 may be about 30 mm. In addition, the width W of the capillary channel 111 may be about 0.4 mm. According to embodiments, the length L of the capillary channel 111 may mean a distance from the inlet 112 in the first direction D1. In addition, the width W of the capillary channel 111 may mean a distance in a second direction D2 that is perpendicular to the first direction D1. Since the length L of the capillary channel 111 is very larger than the width W of the capillary channel 111, a capillary phenomenon may occur. When the capillary unit 110 contacts the sample, the sample may be easily flowed into the capillary channel 111.

The capillary unit 1110 may include a reagent R disposed inside the capillary channel 111. The regent R may be freeze-dried. According to an embodiment, the freeze-dried reagent R may be provided in a membrane type on an inner surface 1110a of the capillary unit 110. In addition, the freeze-dried reagent R may be easily molten by the sample. In other words, the freeze-dried reagent R may easily react with the sample.

The reagent R may develop colors in the sample flowed into the capillary channel 111. The reagent R may include a color-developing material for developing colors in the sample. According to an embodiment, the sample may include an α-amylase. In addition, the reagent R may include a color-developing material of 2-Chloro-4-nitrophenyl-α-D-maltotrioside. 2-Chloro-4-nitrophenyl-α-D-maltotrioside may develop colors in the α-amylase. The sample may further develop colors in 2-Chloro-4-nitrophenyl-α-D-maltotrioside, as the concentration of the α-amylase is higher. The α-amylase may be a biomaterial capable of measuring a stress level. As the user receives more stress, the concentration of the α-amylase included in the sample may be higher.

Unlike this, in another embodiment, the reagent R may further include a catalyst material as well as the color-developing material. The catalyst material may expedite reaction of the color-developing material and the sample. The capillary unit 110 may have first and second pin holes 113 and 114 connected to the capillary channel 111. The first and second pin holes 113 and 114 may be arranged along the second direction D2 perpendicular to the first direction D1.

The first and second pin holes 113 and 114 may face each other. The first and second pin holes 113 and 114 may be disposed adjacent to the other end of the capillary unit 110.

The measuring unit 120 may include an optical sensor 121 and a temperature sensor 122. The optical sensor 121 may measure the degree of color development of the sample to acquire color development information I1. The optical sensor 121 may transmit the acquired color development information I1 to the controller 140. The optical sensor 121 may include a light emitting unit 1211 emitting a light toward the sample inside the capillary channel 111 and a light receiving unit 1212 receiving the light having passed through the sample.

The light emitted from the light emitting unit 1211 may be irradiated inside the capillary channel 111 through the first pin hole 113. The light emitting unit 1211 may be a light emitting diode (LED) but is not limited thereto. The light emitting unit 1211 may be disposed adjacent to the first pin hole 113. The light emitting unit 1211 may overlap the first pin hole 113.

The light receiving unit 1212 may receive a light having passed through the second pin hole 114. The light receiving unit 1212 may be a photodiode but is not limited thereto. The light receiving unit 1212 may be disposed adjacent to the second pin hole 114. The light receiving unit 1212 may overlap the second pin hole 114. The light receiving unit 1212 may convert light energy to electric energy. The light receiving unit 1212 may generate an output voltage corresponding to the intensity of an incident light. For example, the magnitude of the output voltage may be increased as the light intensity increases. The intensity of the incident light may be increased as the degree of color development of the sample is smaller. According to an embodiment, the color development information I1 may include the magnitude of the output voltage generated from the light receiving unit 1212.

According to an embodiment, the light emitting unit 1211, the first pin hole 113, the second pin hole 114 and the light receiving unit 1212 may be disposed along the second direction D2. In other words, the light emitting unit 1211, the first and second pin holes 113 and 114, and the light receiving unit 1212 may be disposed on a virtual straight line. According to an embodiment, the straight line may correspond to a path of the light emitted from the light emitting unit 1211. the light emitting unit 1211, the first pin hole 113, the second pin hole 114 and the light receiving unit 1212 may overlap each other.

The temperature sensor 122 may measure a temperature of the sample to acquire the temperature information I2. According to embodiments, the temperature sensor 122 may be disposed inside the capillary channel 111. In addition, the temperature sensor 122 may be disposed adjacent to the inlet 112. Accordingly, the temperature sensor 122 may swiftly measure the temperature of the sample flowed into the capillary channel 111. The temperature sensor 122 may transmit the acquired temperature information I2 to the controller 140.

The temperature adjusting unit 130 may contact an external side surface 110b of the capillary unit 110. According to an embodiment, the temperature adjusting unit 130 may include a Peltier device. The Peltier device may heat and/or cool the capillary unit 110. Accordingly, the Peltier device may increase and decrease the temperature of the sample inside the capillary channel 111.

The controller 140 may calculate the concentration of the biomaterial included in the sample using the received color development information I1. For example, the controller 140 may calculate the concentration the biomaterial using the magnitude of the output voltage. A detailed description thereabout will be provided in relation to FIGS. 6A and 6B.

The controller 140 may amplify the output voltage using an amplifier (e.g. OP-AMP). In addition, the controller 140 may convert the biomaterial concentration information I3 to a digital signal and transmit the digital signal to the communication unit 160.

The controller 140 may control the temperature adjusting unit 130 using the received temperature information I2. The sample may react best with the reagent R at an activation temperature. For example, the α-amylase may react best with the 2-Chloro-4-nitrophenyl-α-D-maltotrioside at approximately 37 degrees.

The controller 140 may control the temperature adjusting unit 130 such that the temperature of the sample corresponds to the activation temperature. For example, when the temperature of the sample is lower than a preset activation temperature, the controller 140 may control the temperature adjusting unit 130 to raise the temperature of the sample. When the temperature of the sample is higher than the preset activation temperature, the controller 140 may control the temperature adjusting unit 130 to lower the temperature of the sample.

Figure 5:
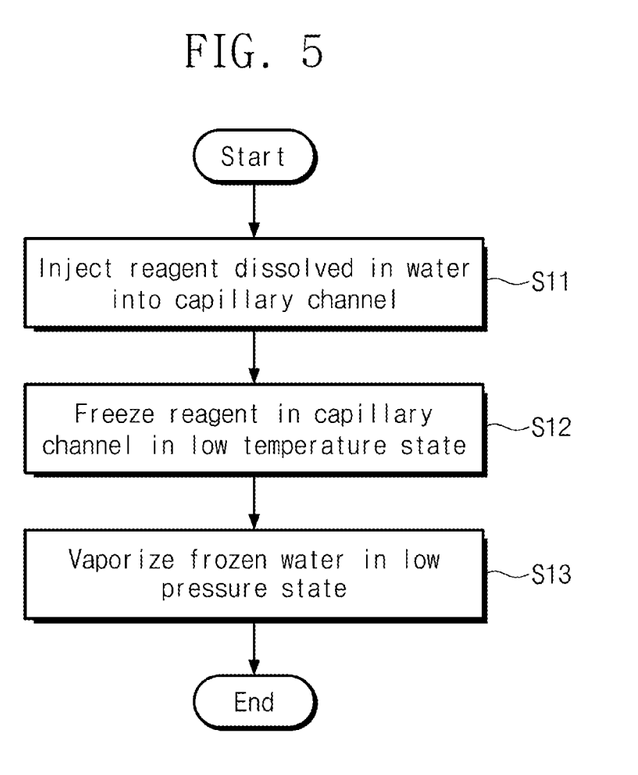
FIG. 5 is a flowchart for explaining a reagent forming process in the capillary channel of FIG. 4.

FIG. 5 is a flowchart for explaining a reagent forming process in the capillary channel of FIG. 4.

Referring to FIG. 5, a reagent dissolved in water (hereinafter reagent solution) may be injected into the capillary channel (step S11). Here, the water may be distilled water, but is not limited thereto. The reagent resolution inside the capillary channel may be frozen in a low temperature state (step S12). For example, the reagent solution may be frozen at about −75° C. for about 2 hours. After being frozen at the low temperature, the reagent solution may be vaporized for about 4 hours using frozen distilled water in a low pressure state (step S13). Accordingly, the reagent may form a membrane on the inner side surface 110a (see FIG. 4) of the capillary unit 110 (see FIG. 4).

Figure 6A:
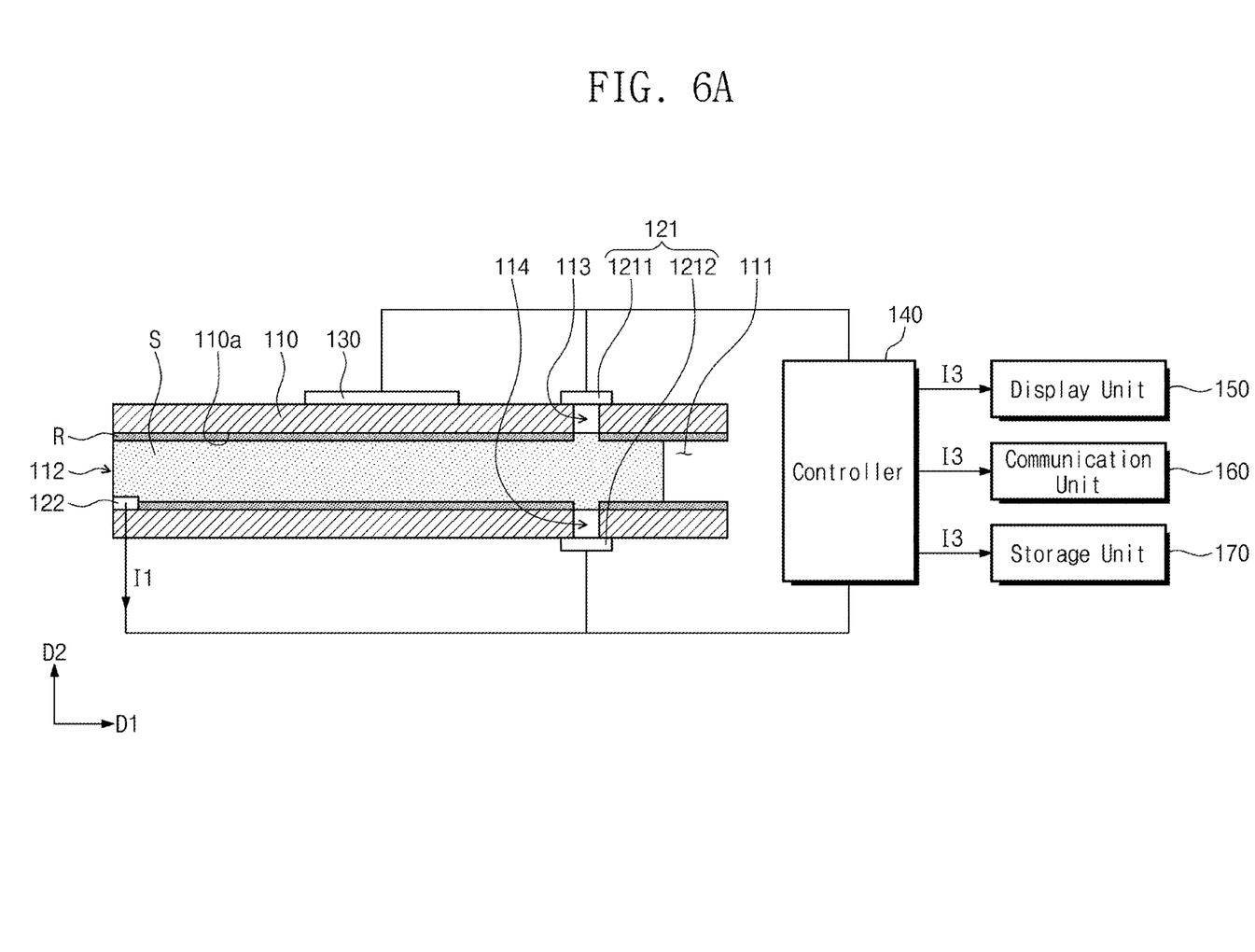
FIGS. 6A and 6B are schematic diagrams for explaining a process in which the biosensor of FIG. 1 analyzes a biomaterial.
Figure 6B:
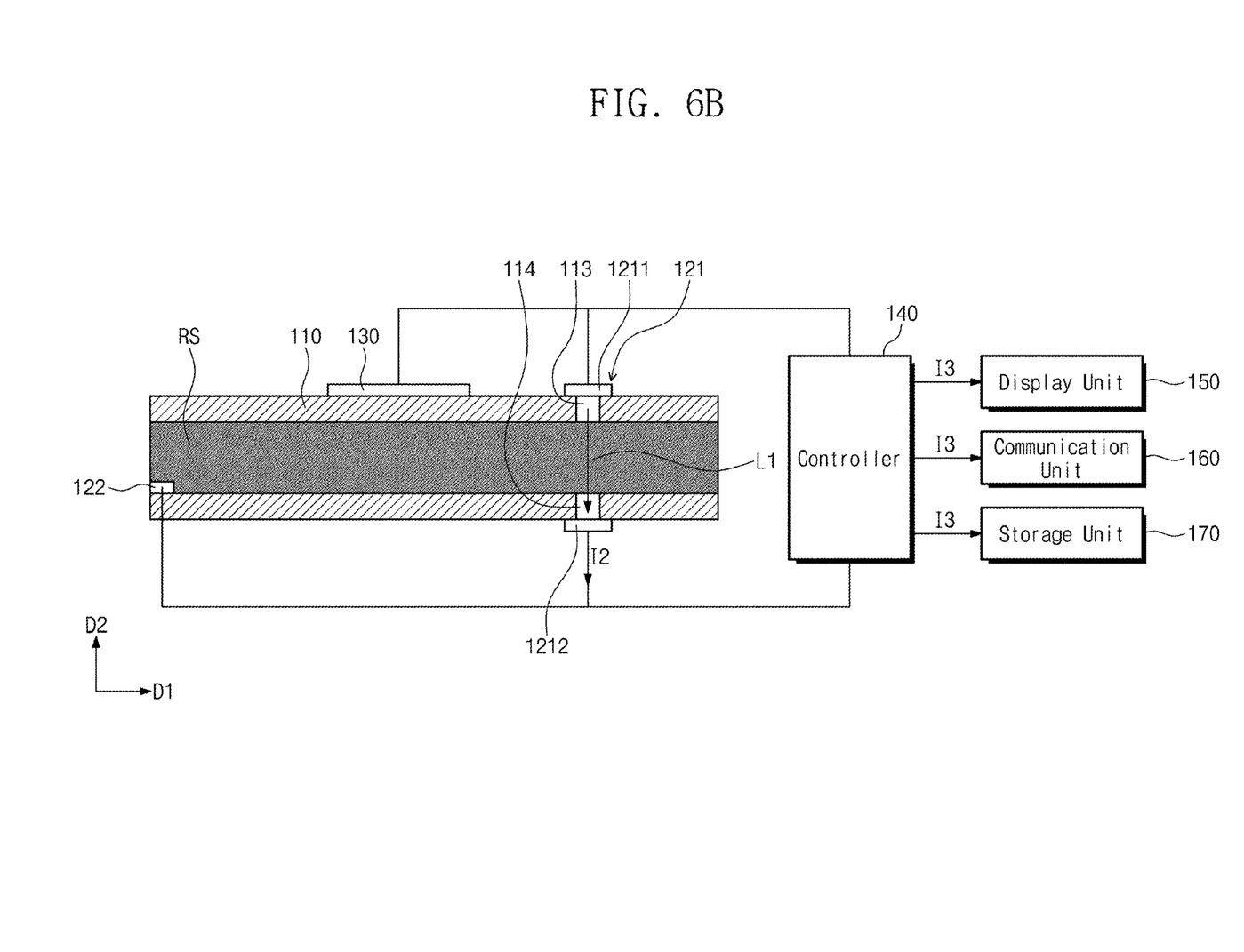
Figure 7:
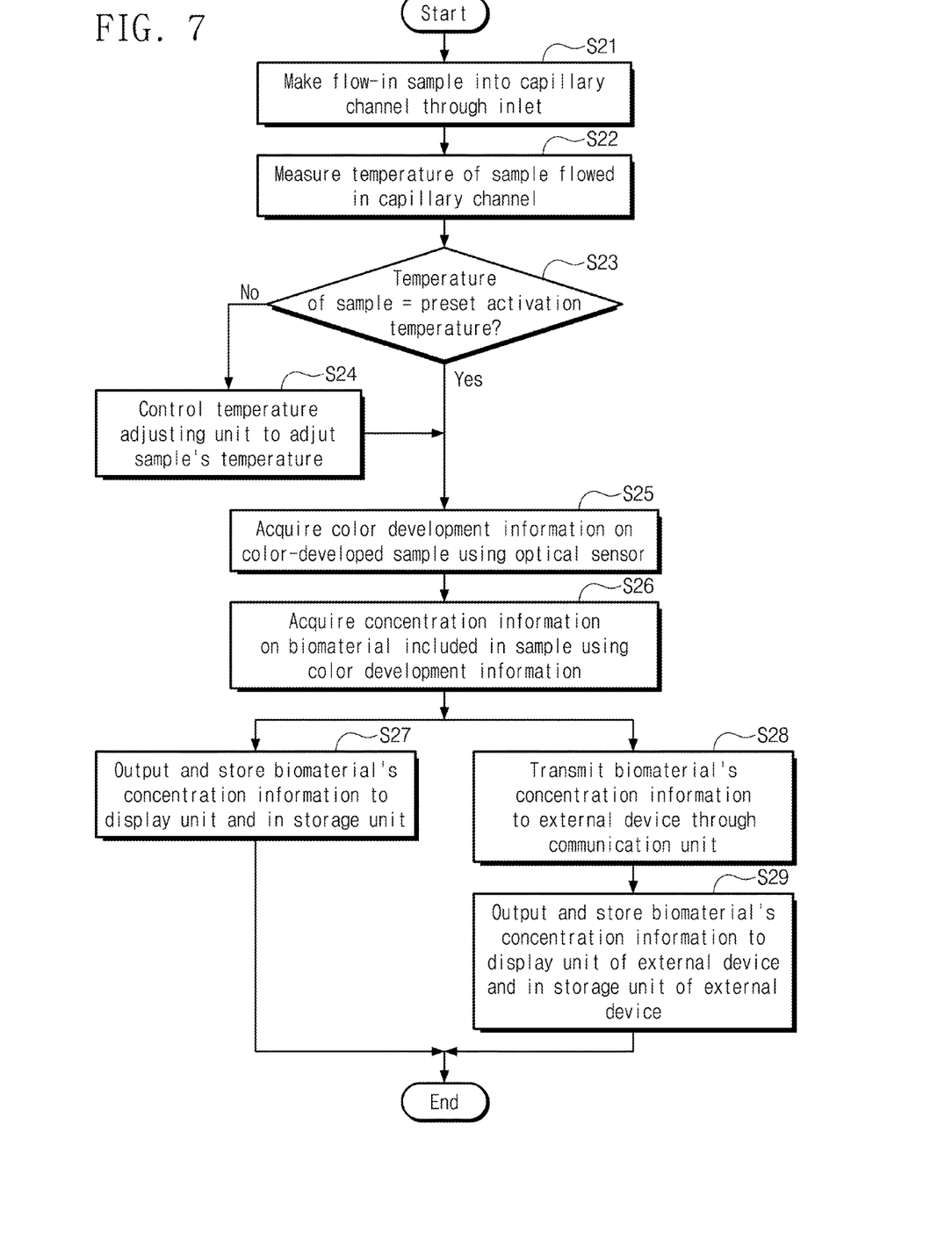
FIG. 7 is a flowchart for explaining a process in which the biomaterial analyzing system of FIG. 1 analyzes a biomaterial.

FIGS. 6A and 6B are schematic diagrams for explaining a process in which the biosensor of FIG. 1 analyzes a biomaterial. FIG. 7 is a flowchart for explaining a process in which the biomaterial analyzing system of FIG. 1 analyzes a biomaterial.

Referring to FIGS. 6A and 7, the sample S may be flowed into the capillary channel 111 through the inlet 112. The sample S may flow in the first direction D1 along the capillary channel 111. The temperature sensor 122 may measure a temperature of the sample S flowed into the capillary channel 111 to acquire the temperature information I1 (step S22). The temperature sensor 122 may transmit the acquired temperature information I1 to the controller 140.

The controller 140 may determine whether the temperature of the sample S correspond to a preset activation temperature (step S23). The controller 140 may control the temperature adjusting unit 130, when the temperature of the sample S does not correspond to the activation temperature. According to an embodiment, the controller 140 may control the temperature adjusting unit 130 to adjust the temperature of the sample S (step S24). Here, that the temperature of the sample S corresponds to the preset activation temperature may mean that the temperature of the sample S is identical to the activation temperature or within an error range.

When the temperature of the sample S corresponds to the activation temperature, reactivity of the sample S and the reagent R may be enhanced. In addition, the sample S may swiftly react with a color-developing material included in the reagent R to develop colors.

Referring to FIGS. 6B and 7, the optical sensor 121 may measure the degree of color development of the color-developed sample to acquire the color development information I2 (step S25).

According to embodiments, the light emitting unit 1211 may emit a light L1 toward the color-developed sample RS. The light L1 may be incident to the color-developed sample RS through the first pin hole 113. The color-developed sample RS may absorb a part of the light L1. The color-developed sample RS may more absorb the light L1, as the degree of color development is larger. The light Li having passed through the color-developed sample RS may be incident to the light receiving unit 1212 through the second pin hole 114. The light receiving unit 1212 may generate an output voltage, when the light L1 is incident. The magnitude of the output voltage may be larger, as the intensity of the incident light L1 is greater. The output voltage generated from the light receiving unit 1212 may be applied to the controller 140.

The controller 140 may acquire the concentration information I3 on the biomaterial included in the sample (step S26). According to embodiments, the controller 140 may compare the magnitude of an applied output voltage with that of a preset voltage to calculate the concentration of the biomaterial included in the sample.

The controller 140 may transmit the biomaterial concentration information I3 to the display unit 150, the communication unit 160, and the storage unit 170.

The display unit 150 may output the biomaterial concentration information I3 and the storage unit 170 may store the biomaterial concentration information I3 (step S27). In addition, the communication unit 160 may transmit the biomaterial concentration information I3 to an external device (step S28).

The external device may output the received biomaterial concentration information I3 to a display unit of the external device. In addition, the external device may store the received biomaterial concentration information I3 to a storage unit of the external device (step S29).

A user may recognize a stress level, or a blood sugar level, etc. through the biomaterial concentration information I3 output to the display unit of the external device and/or the display unit 150 of the biosensor 100.

According to embodiments of the inventive concept, a reagent including a color-developing material may be disposed in a capillary channel. Accordingly, a biomaterial included in a sample may be swiftly measured and analyzed without pre-processing of injecting the color-developing material.

Issues to be addressed in the present disclosure are not limited to those described above and other issues unmentioned above will be clearly understood by those skilled in the art from the following description.

The above-disclosed subject matter is to be considered illustrative and not restrictive, and the appended claims are intended to cover all such modifications, enhancements, and other embodiments, which fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description.

What is claimed is:
1. A biosensor comprising:
a capillary channel and a reagent disposed in the capillary channel, the reagent being configured to develop colors in a sample;

a first pin hole disposed on one side of the capillary channel;

a light source configured to emit light through the first pin hole;

a second pin hole disposed on an opposite side of the capillary channel from the first pin hole, the first and second pin holes penetrating sidewalls of the capillary channel; and a light detector disposed behind the second pin hole and configured to receive light emitted from the light source after it has passed through the first pin hole and the capillary channel and to generate color data from the light;

wherein the first pin hole, the second pin hole, the light source and the light detector are all disposed along a linear axis, and wherein the light detector transmits the color data to a controller that is configured to use the color data to calculate a concentration of biomaterial in the sample, and wherein the first and second pin holes are in fluid communication with the capillary channel.

2. The biosensor of claim 1, wherein the reagent is freeze-dried.

3. The biosensor of claim 1, wherein the reagent comprises a color-developing material configured to develop the colors in the sample.

4. The biosensor of claim 3, wherein the sample comprises an α-amylase, and the color-developing material is 2-Chloro-4-nitrophenyl-α-D-maltotrioside.

5. The biosensor of claim 3, wherein the reagent further comprises a catalyst material configured to expedite a reaction of the color-developing material and the sample.

6. The biosensor of claim 1, further comprising:

a temperature adjusting unit configured to adjust a temperature of the sample in the capillary channel, wherein the measuring unit further comprises a temperature sensor configured to measure the temperature of the sample in the capillary channel.

7. The biosensor of claim 6, wherein the temperature adjusting unit comprises a Peltier device.

8. The biosensor of claim 1, further comprising:

a communication unit configured to transmit the calculated biomaterial concentration information to an external device.

9. The biosensor of claim 8, wherein the communication unit comprises at least any one of a Bluetooth communication module and a Wi-Fi communication module.

10. The biosensor of claim 1, wherein one end of the capillary unit has an inlet connected to the capillary channel.

* * * * *